United States Patent [19]

Hick

[11] 4,424,189

[45] Jan. 3, 1984

[54] PROCESS FOR STERILIZING TUB-SHAPED CONTAINERS

[75] Inventor: Werner Hick, Hiddenhausen, Fed. Rep. of Germany

[73] Assignee: Hick & Co. GmbH, Hiddenhausen, Fed. Rep. of Germany

[21] Appl. No.: 391,246

[22] Filed: Jun. 23, 1982

[51] Int. Cl.³ .................. A61L 2/06; A61L 2/18; A61L 2/20; A61L 2/22

[52] U.S. Cl. .................... 422/27; 422/28; 422/29; 422/297; 422/298; 422/299; 422/302; 422/304

[58] Field of Search .............. 422/27, 28, 29, 297, 422/298, 299, 302, 304, 33

[56] References Cited

U.S. PATENT DOCUMENTS

| 2,014,750 | 9/1935 | Stegemann | 422/304 X |
| 3,421,840 | 1/1969 | Peckmann | 422/304 |
| 3,723,060 | 3/1973 | Lisiecki | 422/302 X |
| 4,296,068 | 10/1981 | Hoshino | 422/304 X |

*Primary Examiner*—Barry S. Richman

[57] ABSTRACT

The sterilization of open-topped containers is accomplished by vaporizing a sterilizing agent in the vicinity of the container. The vaporization is preferably achieved by spraying the sterilizing agent on to a heating element positioned either in or immediately above the open top of the container.

8 Claims, 2 Drawing Figures

PROCESS FOR STERILIZING TUB-SHAPED CONTAINERS

TECHNICAL FIELD

The present invention relates to sterilization and particularly to the destruction of micro-organisms in containers. More specifically, this invention is directed to cleansing apparatus and especially to apparatus for use in the sterilization of open-topped containers. Accordingly, the general objects of the present invention are to provide novel and improved methods and apparatus of such character.

BACKGROUND ART

While not limited thereto in its utility, the present invention is particularly well suited for use as a sterilizing process for killing micro-organisms in containers which are intended to receive food-stuffs. Known processes for sterilizing containers in which food stuffs are to be packaged include UV irradiation, treatment with a mixture of steam and air and the so-called wet aseptic technique in which the interior wall of the container is sprayed with a hydrogen peroxide mixture and subsequently dried. Experience has shown peroxide to be a particularly reliable sterilizing agent for killing micro-organisms and containers subjected to the wet aseptic technique may accordingly be used when a long shelf life is required.

The germicidal action of peroxide depends upon the formation free oxygen, the free oxygen being formed during thermal decomposition and exhibiting a particularly strong sterilizing effect at the moment of formation. The efficiency of a wet aspetic process is also attributable to the liquid hydrogen peroxide which penetrates the cell coatings of the micro-organisms.

Under the best of circumstances, i.e., with the finest nebulisation, only thirty-five percent of the internal surface of a container can be wetted by an atomized hydrogen peroxide mixture. The inability to completely wet the surface of the container to be treated is attributable to the fact that droplets form on the surface and unwetted areas remain between these droplets.

Since peroxide is a toxic substance, it is necesary to remove substantially all residues of peroxide from containers treated by a wet aseptic process. The removal of the peroxide is achieved by evaporation and thus a wet aseptic process requires, subsequent to the spraying step, a heating step. The combined spraying and heating steps, however, do not result in absolute sterilization of the entire internal surface of a treated container.

DISCLOSURE OF THE INVENTION

The present invention overcomes the above-discussed and other deficiencies and disdvantages of the prior art by providing a reliable wet aseptic process for sterilization of the entire internal surface of a container in a single step operation. In accordance with the invention a sterilizing agent, preferably a hydrogen peroxide mixture, is vaporized either within the container to be sterilized or immediately in front of the container to provide free oxygen in the container, the vapor condensing on the wall of the container as a film. The vaporization of the sterilizing agent is caused to occur in a substantially instantaneous manner and the condensate wets the entire internal surface of the container being sterilized. Significantly improved sterilization occurs because of the wetting and also because instantaneous thermal decomposition of the hydrogen peroxide results in a vapor having, because of the significant quantity of free oxygen present, greater germicidal activity when compared to hydrogen peroxide in its liquid phase. The present invention is a one-step procedure in that it is unnecessary to perform any treatment steps particularly an evaporation step, to remove residues of hydrogen peroxide from the container.

The present invention also encompasses apparatus for use in the practice of the above-described novel process.

BRIEF DESCRIPTION OF DRAWING

The present invention may be better understood and its numerous objects and advantages will become apparent to those skilled in the art by reference to the accompanying drawing wherein like reference numerals refer to like elements in the two figures and in which.

BEST MODE OF CARRYING OUT THE INVENTION

Figure 1:
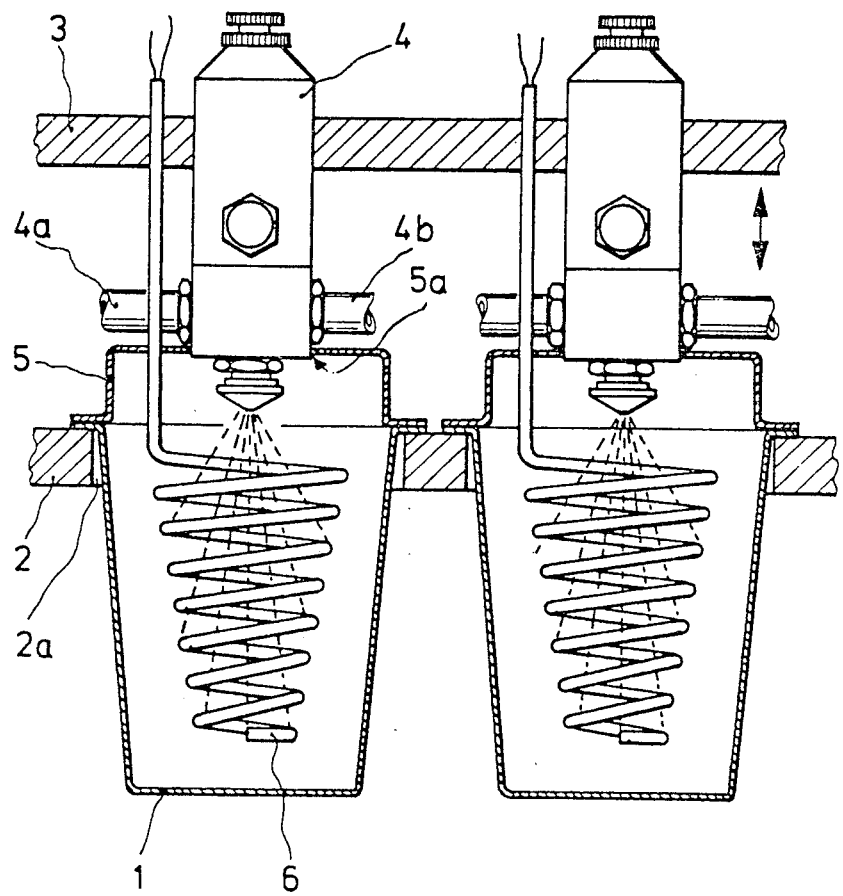
FIG. 1 is a schematic, cross-sectional side elevation view of apparatus in accordance with a first embodiment of the invention.

Referring to FIG. 1, a conveyor for transporting tubs 1 which are to be sterilized is indicated at 2. The conveyor 2 is provided with plural recesses 2a in which the tubs 1, which for example may be intended to be filled with dairy products, are supported by the lip flanges provided on the tubs. A vertically movable support 3 is positioned above conveyor 2 and supports a plurality of spray nozzles 4, the nozzles 4 being positioned so as to be centered with respect to the conveyor recesses 2a. Each of nozzles 4 is connected, via a conduit 4a, to a source of compressed air and, by a conduit 4b, to a reservoir which contains a mixture of hydrogen peroxide or other suitable sterilizing agent.

During the sterilization procedure the open ends of the tubs 1 are closed by means of caps 5 which are mounted on and hermetically sealed to the nozzles 4 as indicated at 5a. Thus the caps are provided with peripheral flanges which are urged tightly against the lip flanges of the tubs by the descending motion of the support 3. The discharge ends of the nozzles 4 project into the chambers defined in part by the caps 5.

A heating coil 6 is supported from and extends below each of the nozzles 4. In the embodiment depicted in FIG. 1 the tubs to be sterilized are of frutoconical shape and thus the heating coils 6 are in the shape of truncated cones which project into the tubs so as to be spaced a predetermined distance from the base and wall thereof. The coils 6 are connected to a source of electric current.

As noted above, the support member 3, and thus the nozzles 4 and heating coils 6, are movable vertically with respect to conveyor 2, this movement being indicated by the double headed arrow. The rate of vertical movement of the support 3 is synchronized with the advance of the rows of tubs whereby the heating coils are lowered briefly into previously untreated tubs, the tops of the tubs are sealed by the caps 5 and the sterilization treatment is performed.

With the heating coils positioned within the tubs, as shown in FIG. 1, the spray nozzles are actuated and extremely fine droplets of a hydrogen peroxide mixture are sprayed into the tubs. The spray impinges on the heating coils, which have a surface temperature of approximately 500° C., whereupon the liquid undergoes an immediate transition to the gas phase. The free oxygen thus produced has a potent germicidal action and the vapor subsequently precipitates as a condensate film on the internal wall of the tub whereby an absolutely reliable germicidal effect is achieved. In a preferred embodiment of the invention the hydrogen peroxide mixture employed consisted of a 35% concentration of hydrogen peroxide.

Figure 2:
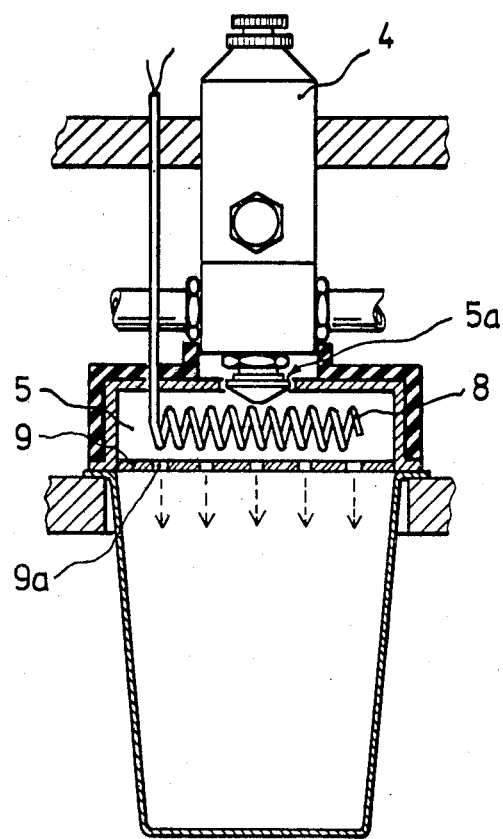
FIG. 2 is a schematic, cross-sectional side elevation view of apparatus in accordance with a second embodiment of the invention.

An alternative technique in accordance with the invention is depicted in FIG. 2. In the process of FIG. 2 the vaporization of the sterilizing agent is effected immediately above the container to be sterilized. Thus, apparatus for use in the practice of this alternative technique employs a heating coil 8 which is positioned entirely within the cap 5, the sterilizing agent being sprayed into the chamber defined by the cap. In order to prevent loss of heat, the cap is preferably provided with a covering of a suitable insulating material as shown. Additionally, in the FIG. 2 embodiment the cap 5 is provided with a bottom plate 9 provided with one or a plurality of apertures 9a, the apertures serving the purpose of increasing the flow velocity of the vaporized sterilizing agent to the container to thereby achieve an optimum distribution of the vapor.

While preferred embodiments have been shown and described, various modifications and substitutions may be made thereto without departing from the spirit and scope of the invention. Accordingly, it is to be understood that the present invention has been described by way of illustration and not limitation.

I claim:

1. An improved technique for the sterilization of the internal surfaces of an open-topped container comprising the steps of:
   atomizing, in the vicinity of a container to be sterilized, a sterilizing agent capable of the formation of free oxygen upon thermal decomposition;
   directing the atomized sterilzing agent against a high temperature surface located in the immediate vicinity of said container to cause substantially instantaneous thermal decomposition thereof whereby free oxygen is formed; and
   permitting the vapor resulting from the thermal decomposition of the sterilizing agent to condense on the internal surfaces of the container and to subsequently evaporate therefrom, whereby the combined effects of the free oxygen and condensed sterilizing agent vapor causes sterilization of said internal surfaces.

2. The method of claim 1 wherein the step of directing the atomized sterilizing agent against a high temperature surface includes:
   positioning the high temperature surface upstream of the bottom of the container to be sterilized in the direction of travel of the atomized sterilizing agent.

3. The method of claim 2 wherein the step of positioning the high temperature surface comprises:
   locating an electric heating element adjacent the open top of the container.

4. The process of claim 3 further comprising the step of:
   employing the container to be sterilized to define a substantially air-tight cavity, the heating element being disposed within the said cavity.

5. The process of claim 4 wherein the heating element is at least partly positioned within the void defined by the internal surfaces of the container when the sterilizing agent is directed thereagainst.

6. The process of claim 5 wherein the sterilizing agent is a hydrogen peroxide mixture.

7. The process of claim 4 wherein the heating element is positioned above and in registration with the open top of the container when the sterilizing agent is directed thereagainst.

8. The process of claim 7 wherein the sterilizing agent is a hydrogen peroxide mixture.

* * * * *

UNITED STATES PATENT AND TRADEMARK OFFICE
CERTIFICATE OF CORRECTION

PATENT NO. : 4,424,189
DATED : January 3, 1984
INVENTOR(S) : Werner Hick

It is certified that error appears in the above—identified patent and that said Letters Patent are hereby corrected as shown below:

On the Title page, insert:

[30] Foreign application priority data

June 27, 1981 [DE ] Fed. Rep. of Germany 3125430

Signed and Sealed this

Fourteenth Day of October, 1986

[SEAL]

*Attest:*

DONALD J. QUIGG

*Attesting Officer*      *Commissioner of Patents and Trademarks*